United States Patent [19]

Hatschek

[11] Patent Number: 4,890,619

[45] Date of Patent: Jan. 2, 1990

[54] SYSTEM FOR THE MEASUREMENT OF THE CONTENT OF A GAS IN BLOOD, IN PARTICULAR THE OXYGEN SATURATION OF BLOOD

[76] Inventor: Rudolf A. Hatschek, P.O. Box 64; 3, rue Jacques-Vogt, CH-1700 Fribourg, Switzerland

[21] Appl. No.: 38,296

[22] Filed: Apr. 14, 1987

[30] Foreign Application Priority Data

Apr. 15, 1986 [CH] Switzerland ............... 1497/86
Apr. 15, 1986 [CH] Switzerland ............... 1498/86

[51] Int. Cl.$^4$ ............................................. A61B 5/00
[52] U.S. Cl. ................................... 128/633; 128/24 A
[58] Field of Search .................... 356/39–41; 128/633, 661.04, 635, 24 A

[56] References Cited

U.S. PATENT DOCUMENTS 2,691,889 10/1954 Dion et al. ..................... 374/115
4,058,975 11/1977 Gilbert et al. ................. 374/110 X
4,086,915 5/1978 Kofsky .......................... 356/41 X

FOREIGN PATENT DOCUMENTS 2530834 2/1977 Fed. Rep. of Germany.
2823769 12/1979 Fed. Rep. of Germany.
8008137 3/1980 Fed. Rep. of Germany.

OTHER PUBLICATIONS

Dictionary of Electronics; GRAF, 1973, p. 483.

Technique of Ultrasonic Therapy, British Journal of Physical Medicine, 7/1951, Bauer.

Primary Examiner—William E. Wayner
Attorney, Agent, or Firm—Spencer & Frank

[57] ABSTRACT

The system comprises a mounting device and two holding members detachably fastened to the mounting device, each holding member comprising a measuring head. Each measuring head comprises a light receiver and light sources adapted to emit light signals at various wave lengths and at least one heat radiator adapted to heat the bodily region, and particularly the skin region in which the oxygen saturation of the blood is measured, by the irradiation of waves. If the two measuring heads are positioned during measurement on opposite sides of the bodily part to be examined, then each light receiver will be able to receive reflection light dispersed back from the bodily part as well as transmission light permeating through the bodily part, thus yielding a good measurement accuracy. The power output of the waves emitted by the radiator is controlled by pulse width control in a way to have a parameter representing a measure for the heart pulse cause changes in the intensity of light coming out of the body and reaching at least one of the light receivers so as to have a predetermined desired value. An adequate heating of the bodily region is thus guaranteed, without any tissue damages occurring due to overheating.

19 Claims, 4 Drawing Sheets

SYSTEM FOR THE MEASUREMENT OF THE CONTENT OF A GAS IN BLOOD, IN PARTICULAR THE OXYGEN SATURATION OF BLOOD

BACKGROUND OF THE INVENTION

1. Field of the Invention

The present invention concerns a new and improved system for the measurement of the gas content of blood of a living being in a region of its body, and particularly for the optical measurement of the oxygen saturation of blood flowing through said region of the body. Systems of this kind are used for example for noninvasively determining the oxygen saturation of blood, i.e. without any instruments to penetrate through the skin or through any other bodily surface, in patients having disturbed oxygen supply as a consequence of sickness or of surgical operations or during the medical examination of athletes. The term oxygen saturation shall be understood to mean the degree of saturation of hemoglobin with oxygen or, more precisely, the ratio between the concentration of the hemoglobin comprising oxygen, known as oxyhemoglobin, and the total concentration of hemoglobin. The oxygen saturation is usually expressed in percent of the maximum saturation and is often referred to as SA or $SaO_2$.

2. Description of the Prior Art

The process of noninvasive optical measurement of oxygen saturation of blood is based upon the fact, that hemoglobin with bound oxygen, i.e. the oxyhemoglobin, and hemoglobin containing little or no oxygen, known as desoxyhemoglobin, have dissimilar colors and therefore dissimilar absorption spectra. The measurement is generally performed by radiating light of two or more dissimilar wave lengths into a bodily region containing blood vessels and particularly capillary tubes. Then the intensity of light penetrating through said bodily region, such as an ear lobe, the tongue, or a finger, or the luminous intensity of the light reflected back from said bodily region, in particular from the skin thereof, is determined.

Information regarding the measurement principle involved has been known for example from the publication entitled "Noninvasive Transcutaneous Monitoring of Arterial Blood Gases" by Y. Mendelson and R. A. Peura, which appeared in the IEEE Transactions on Biochemical Engineering, Vol. BME-31, No. 12, 1984 on page 792ff. One of the systems for measuring oxygen saturation described in this Publication comprises a measuring head to be set in place in a particular location on the surface of the body. This measuring head is equipped with light emitting diodes adapted to radiate red and infrared light into the respective region of the body, furthermore a photodiode adapted to receive light reflected from the tissue of said region, and a heating device form of a copper ring. During the measuring process the copper ring rests with one of its faces on the skin surface and supplies the skin with heat generated by a heating coil. By applying heat to the region to be checked for its oxygen saturation it is possible to increase the blood supply by as much as twenty to thirty times. This improves the accuracy of measurement, or makes the measurement possible in the first place. A conclusion that may be drawn from the publication under discussion is that an advantageous value for the temperature of the bodily region to be checked for its oxygen saturation is approximately 41°.

It is furthermore known, that the skin parties, and particularly the skin cells, as well as the tissue cells lying deeper can get damaged at temperatures higher than 42° C., the survival time of the cells being subject to considerable decrease as the temperature rises above 42° C. The skin covering the body may be subdivided into the outer epidermis and the inner dermis, the latter containing blood vessels. The epidermis, on the other hand, possesses living cells below its lifeless horny layer (stratum corneum) but no blood vessels. When heating the dermis with its blood vessels by the heat it receives from the skin surface by heat conduction, a temperature gradient will arise from the outside toward the inside. The horny layer varies in thickness in different parts of the body, typically between 0.2 and 2 mm, the thickness of the horny layer also depending on the age and the living conditions of the person to be examined. Thus, this known system has the disadvantage, that two possible risky conditions may occur, depending on the value of the temperature generated at the surface of the skin by means of the heating device. In one case, the skin tissue containing the blood vessels may fail to get heated to the temperature required for good measuring conditions, in the second case parts of the skin may become overheated, so that tissue damage may result.

Other known systems are equipped with two dissimilar measuring heads, one of these being provided with light sources and the other with a light receiver. Thus, the first measuring head is adapted to radiate light through a bodily part, the second being adapted to receive this light. These known systems are thus suited for measurement processes in which only light radiated from the examined bodily region back into the measuring head from which it originates, is used, or only light which has penetrated through the bodily part to be checked. Furthermore, the measuring heads of the systems using light to penetrate the bodily part are so built and supported, that they may be used practically exclusively for measurements to be performed on a specific part of the body, such as an ear lobe or a finger. The physician is thus limited to performing his measurements only with light reflected back from the checked bodily region, or only with light penetrating through a bodily part, such as an ear lobe or a finger. As an alternative he would have to buy several different systems adapted for the different types of measurements. Also, in the systems working with light penetrating through the part of the body checked, the light signals reaching the light receivers have light intensities frequently so low, that the results of measurements are quite inaccurate and unreliable.

SUMMARY OF THE INVENTION

Hence from what has been explained heretofore it should be apparent that the art is still in need of systems for the noninvasive transcutaneous measurement of the content of a gas in blood and particularly for the optical measurement of the oxygen saturation of blood which are not associated with the aforementioned drawbacks and limitations of the state-of-the-art proposals.

It is therefore a primary object of the present invention to provide a novel system for the noninvasive transcutaneous measurement of the gas content of blood and particularly the optical measurement of oxygen saturation of blood, which is not associated with the drawbacks and limitations of the prior art as heretofore discussed and which effectively and reliably fulfills the existing need in the art.

Another and more specific object of the present invention relates to a new and improved system, which makes it possible to heat a region of the skin and/or another bodily region comprising blood vessels to a temperature high enough to sufficiently stimulate the supply of blood for the accurate noninvasive measurement of the gas content of blood flowing through said region and particularly of the oxygen saturation of the blood, without damaging the respective region and/or its neighboring bodily regions by overheating.

Yet a further significant object of the invention relates to a novel and versatile system which can be used for many different types of optical measurements of oxygen saturation and particularly for performing measurements using light penetrating through said bodily part, the measurements yielding accurate and reliable results even under unfavourable conditions.

The foregoing and other objects are attained in accordance with one aspect of the present invention through the provision of radiating means adapted to radiate waves into said region of the body for heating said region.

Other features of the invention will become evident from the subclaims dependent on the main claim.

A few of the advantages of the system of the invention are described in the following. The system may comprise for example one or more radiators for radiating light waves, i.e. electromagnetic waves, or one or more radiators for radiating ultrasonic waves into the bodily region, in which the gas content of the blood flowing through is measured. The bodily region may be heated by means of the radiated waves to a temperature adapted to increase blood circulation, while avoiding any damaging overheating of tissue in said bodily region and/or in the regions adjacent thereto.

As mentioned before, the system may be adapted for the measurement of oxygen saturation of blood. In this case the system may comprise one or more light receivers as well as light emitting means adapted to emit light of two or more dissimilar wave lengths into said bodily region, the light to serve for the measurement of oxygen saturation. If the radiator serving for heating said bodily part is implemented as a light radiator, then the light radiated by the latter may be used either for heating only, or for the measurement of oxygen saturation also. In the first case the light radiator is not part of the light emitting means serving for the measurement proper, whereas in the second case it is very much part of it. The device may comprise one measuring head, or preferably two measuring heads. The measuring head, or each measuring head, as the case may be, preferably comprises a support having an outer shell bounding a hollow space, the latter being open—during measurement—on the side of the measuring head making contact with the body of a living being. The light radiation means may comprise light sources disposed within said hollow space of the measuring head and preferably consist of light diodes. One or more radiators could then be assigned to the measuring head, or to each measuring head, as the case may be. If the radiator, or each radiator, as the case may be, is implemented as an ultrasonic radiator, then it may also be accommodated within the hollow space of the measuring head. If the radiator, or each radiator, as the case may be, is implemented as a light radiator, then it may be mounted within or on the measuring head, and/or optically connected with the same.

Instead of measuring the oxygen saturation, the system may be adapted for measuring the content of a blood gas other than oxygen, for example carbon dioxide. A measurement of this kind could then be carried out on the basis of a noninvasive process different from the optical process. Some such processes have been known from the previously cited publication by Y. Mendelson and R. A. Peura. In a measurement of this kind it could also be of advantage, to increase the blood supply of a bodily region by irradiating the latter with waves.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figures 1, 2, 3:
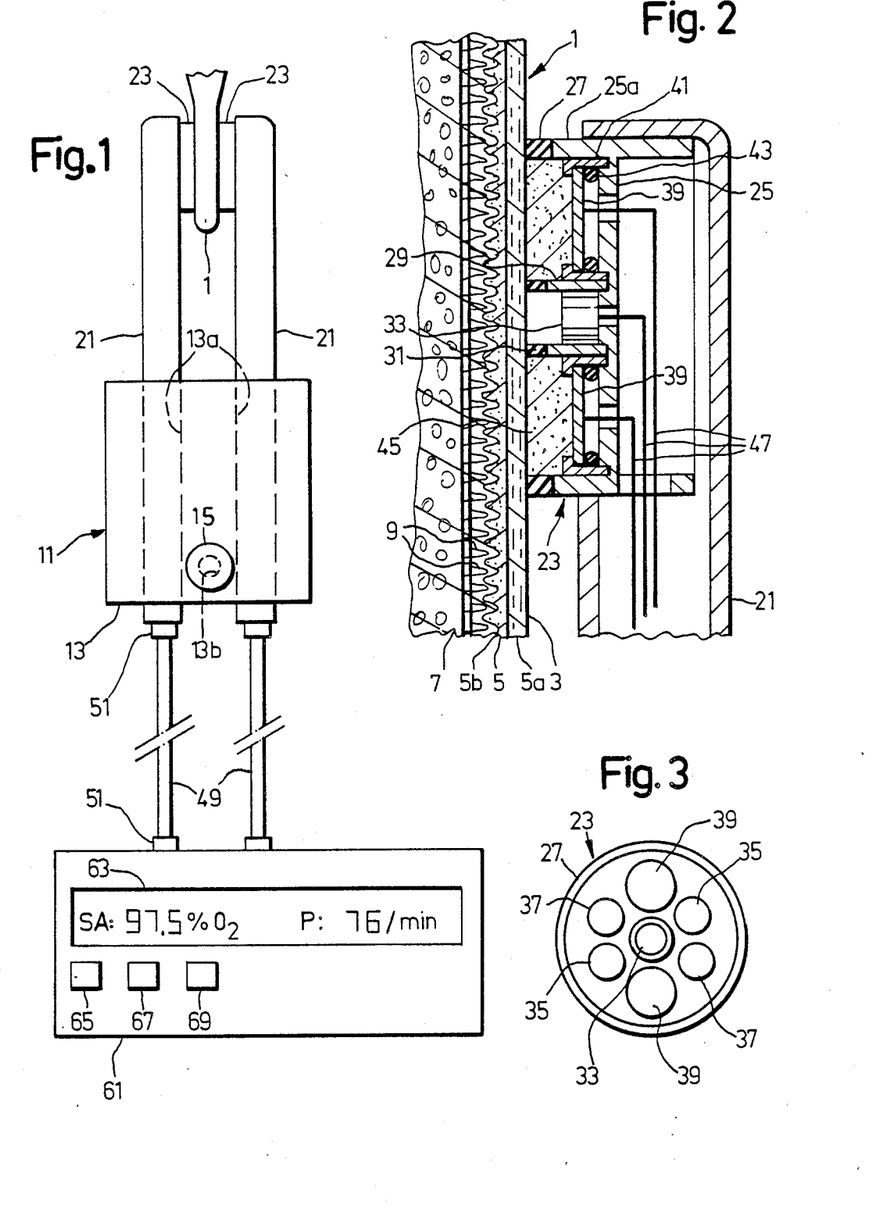
FIG. 1 shows a bodily part and a schematic view of a system for measuring oxygen saturation of blood.
FIG. 2 shows a schematic section through a piece of skin and through a measuring head brought in contact with the skin, at a larger scale.
FIG. 3 shows a top view of the side of a measuring head destined to be brought into contact with the skin, at a scale smaller than FIG. 2.

FIG. 1 shows a schematic view of a bodily part 1, for example an ear lobe, and a system for measuring the oxygen saturation of the blood passing through said bodily part 1. The system comprises at least one mounting device 11 having as its main component a rubber-elastic block 13 comprising two through holes 13a running essentially parallel to each other. Each of these through holes 13a has an elongated, arm-like, hollow holding member 21 of rectangular cross-section snugly inserted into it. Stop means could also be provided for setting the depth of the insertion. The block 13 comprises in the vicinity of its one edge a through hole 13b located between the two through holes 13a running perpendicular to the same. An adjusting member 15 comprises a headed screw, a shaft permeating the through hole 13b and a nut screwed onto the threaded part of the screw.

Each holding member 21 has a measuring head 23 mounted at the terminal segment thereof which faces away from the mounting device 11, the measuring head being arranged to protrude from one of the longitudinal sides of the holding member 21. The two measuring heads are constructed essentially identical and—in the arrangement shown in FIG. 1—they are facing toward opposite sides of the bodily part 1. The block 13 may be pressed together by means of the adjusting member 15 and deformed to a greater or lesser extent. As a result, the two holding members 21 which ran for example parallel to each other as long as the block 13 was undeformed, will now change their directions relative to each other. Thus, it is possible, within certain limits, to adjust the relative distances of the two measuring heads 23—by means of the adjusting member 15—to the thickness of the bodily part 1 which—for carrying out the measurement—must be placed between the two measuring heads, so as to make the latter make contact—during the measuring process—with the sides of the bodily part 1 that face away from each other.

FIG. 2 shows a schematic illustration of a piece of skin constituting the outer covering of the bodily part 1 and comprising several layers as parts of the epidermis 5 and the dermis. The epidermis comprises the horny layer 5a located on the outside and lacking life and blood vessels, and the germinant layer 5b equally lacking blood vessels but comprising living cells. On the inside the epidermis is separated from the dermis 7 by a boundary surface wave-shaped in cross-section. The dermis comprises living cells and blood vessels 9, n particular loop-shaped capillaries. The dermis 7 is adjoined—without any sharp boundary—by the subcutaneous tissue which comprises both living cells and blood vessels. As shown in FIG. 2 the measuring head 23 comprises a support 25 provided with a plate-shaped portion and a ring-shaped, i.e. cylindrical shell 25a of stable shape. At its edge adjacent to the holding member 21 the outer shell 25a is provided with a gasket 27 consisting of a rubberlike elastic material, such as foam rubber. A sleeve 29 is fixedly mounted on the support 25 in the central region of the plate-shaped support portion and coxial to the shell 25a. The cylindrical shell of the sleeve 29 is equally provided with a gasket 31 at its free edge. The free edges of the two gaskets 27, 31 are located in a common plane running parallel to the longitudinal direction of the holding member 21 and are adapted to be brought into tight contact with the surface of the skin 3 while the system is in use. A photoelectric light receiver 33, such a silicium photo-element or a photodiode is fixedly mounted within the sleeve 29. Serving together as light emitting means are the light sources 35, 37 shown in FIG. 3, specifically gallium aluminum arsenide photodiodes, mounted in the inside space of a chamber limited by the plate-shaped portion of the support 25 and the shell 25a. The light sources 35, 37 are arranged in pairs symmetrically with respect to the axis of the outer shell 25a and of the light receiver 33. Furthermore, the inside space bordered by the outer shell 25a accommodates the radiating and heating means comprising one or more ultrasonic radiators 39, for example two ultrasonic radiators 39 symmetrically disposed in relation to the axis of the outer shell 25a and of the light receiver 33. Each of the ultrasonic radiators consists of a circular plate-shaped piezoelectric element held in a sleeve 41 fixedly mounted on the support 25, and is sealed by means of a ring-shaped seal 43, such as an O-ring. The hollow space provided within the shell 25a, between its inner surface, the sleeve 29 and the side of the radiator 39 facing the skin 3 accomodates an ultrasonic wave transmitter 45 comprising a gelatinous filler mass consisting of polyethylene-glycol and being pervious to visible and infrared light, said filler mass being arranged to also cover the radiating sides of the light sources 35, 37 facing the skin during the measuring process.

Figure 4:
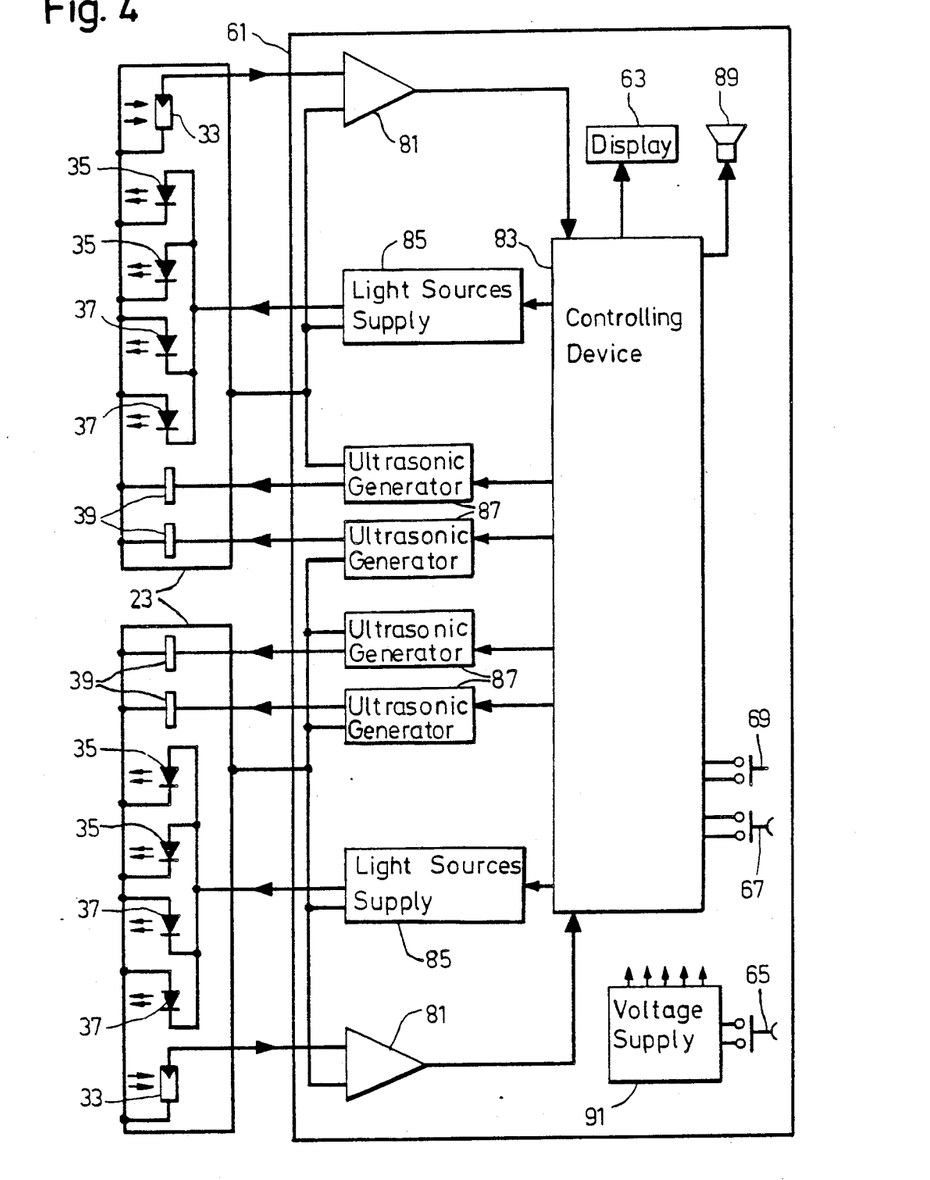
FIG. 4 shows a block diagram of the system.

The electrical elements, i.e. the light receivers 33, the light sources 35, 37 and the ultrasonic radiators 39 have for example a common connection connected with the metallic parts of the support and wall means of the measuring head 23 and holding member 21, and are electrically connected by way of the conductors 47 and a cable 49 with the electronic apparatus 61 schematically shown in FIG. 4. The cables 49 comprise—preferably at least at one of their ends—connectors 51 adapted to make the cables 49 separable from the measuring heads 23 and the holding members 21 supporting them, and/or from the electronic apparatus 61. The apparatus 61 comprises electronic circuit means, a display member 63 for the digital display of oxygen saturation of the blood, more specifically the degree of oxygen saturation SA in percent, and the pulse frequency P. The apparatus 61 furthermore includes various switches which may be actuated manually and which comprise for example pressure keys, specifically an on-off switch 65, a test switch 67 for testing and calibrating the apparatus, an alarm switch 69 for activating the alarm signalizer and possible additional switches not shown.

As shown in FIG. 4 the electronic circuit means of the apparatus 61 comprise for each light receiver 33 an amplifier adapted to connect the respective light receiver 33 with a controlling device 83. The device 83 comprises, among others, circuit means for analog signal processing, analog to digital converters for converting the electrical analog signals coming from the amplifiers 81 into digital signals, a clock, and a digital computer such as a microprocessor. The photodiodes serving as light sources 35 and the photodiodes serving as light sources 37 are electrically connected with opposed polarities in parallel, and are connected with a light source supply device 85 associated with the respective measuring head. Instead of two separate supply devices 85 there may be provided one single supply device common to both measuring heads. Each ultrasonic radiator 39 is connected to an ultrasonic generator 87. The supply device 85 and the generator 87 are connected to the controlling device 83 and adapted to be controlled in a manner to be explained later. The controlling device 83 is furthermore electrically connected to the display component 63, the switches 67, 69 and an acoustical alarm signalizer 89 mounted into the apparatus 61. Instead of or in addition to the acoustical signalizer 89 there may be provided an optical alarm signalizer integrated into the apparatus 61, and/or an external acoustical and/or optical alarm signalizer. The apparatus 61 furthermore comprises a voltage supply means 91 connected to an on-off switch and provided for example with at least one battery and/or mains connection and being adapted to generate the electrical DC-voltages required by the various electronic circuits and devices of the apparatus 61.

The operation of the system will now be explained under the assumption, that a bodily part 1 to be checked for oxygen saturation in its blood, for example the ear lobe of a person, is positioned between the two measuring heads 23 in the manner shown in FIG. 1, in a way to have the measuring heads 23 come in contact with the skin surface through the gaskets 27, 31. If the apparatus 61 is switched on for making a measurement, then the controlling device 83 will exert control over the supply devices 85 for the light sources, in a way to make them generate periodic electrical pulse sequences with pulses having alternatingly different polarities, with the result, that in response to the first category of electrical pulses it will be the light sources 35, and in response to the second category of pulses it will be the light sources 37 which will generate light signals or light pulses. The frequency of light signals or pulses is to be considerably higher than the human pulse or heart beat frequency, and shall have for example a minimum value of 70 Hz and a maximum value of 150 Hz. Attention shall be paid to have the frequency of the light signals different from the frequency, or from an integer multiple of the frequency of the line voltage available in the geographical area in which the system is operated, to keep disturbances by the AC-line voltage and/or by the light emitted by lamps energized by the AC-line voltage at low levels. At the same time the two supply devices 85 are controlled in a way to make the pulse sequences generated by them not only synchronous, but also in phase with each other, making all of the light sources 35 of both measuring heads generate their light signals at the same time, the same being true for the light sources 37.

The light generated by the light sources 35, 37 lies in the visible and/or the near infrared range. The light source 35 may generate for example light of a wave length lying in the vicinity of the so called isobestic point, a point at which the absorption curves of hemoglobin containing oxygen and hemoglobin lacking oxygen mutually cross, a wave length referred to in the following as isobestic wave length and having a value of 805 nm. At the same time the light sources 37 may generate for example light having a wave length larger or smaller, by 50 to 300 nm for example.

If light generated by one of the light sources 35, 37 penetrates into said bodily part 1, then the light may become absorbed or dispersed into various directions, specifically, approximately in the forward or backward direction, while one part of the light may just permeate through the bodily part 1 without any deviation.

It the two measuring heads 23 are arranged to face each other as shown in FIG. 1, then each light receiver 33 may receive light generated by the light sources 35, 37 of its own measuring head 23 and reflected back by the bodily part 1 through dispersion, as well as light generated by the light sources 35, 37 of the other measuring head 23 and which has permeated the bodily part 1. In the following we will refer to the light which reaches a light receiver while originating from the light sources of the same measuring head as reflection light, and the light which reaches the light receiver while originating from the light sources of the second measuring head as transmission light. By the way, the sleeves 29 and the gaskets 31 enclosing the light receiver 33 guarantee that each light receiver will receive only such reflection light, as has penetrated at least into the skin 3 of the bodily part 1.

The light receivers 33 generate an electrical signal in response to each light signal they receive from the bodily part 1, specifically a voltage pulse of a magnitude representing a measure for the light intensity. At the same time the light intensities of the reflection light signals and those of the transmission light signals entering a light receiver simultaneously will become added, resulting in relatively large light intensities and voltage pulses, and correspondingly good measuring accuracies. The controlling device 83 possesses electronic pathways realized by means of gate circuits and/or by other means, for identifying and sorting the signals it receives from the light receiver 33 by way of the amplifiers 81 on the basis of their time sequenced arrival, and to assign them to the two light wave lengths. The computer of the controlling device 83 then calculates the oxygen saturation, for example for each of the two light receivers 33, on the basis of the sequence of signals emitted by them, then determines the average value and feeds the corresponding signals to the display member 63, to make the latter display the average value of oxygen saturation of the two measurement channels. Forming an average value in this way increases the accuracy of measurement. Provisions could also be made, however, to have the oxygen saturation values measured in the two measurement channels displayed alternatingly or perhaps simultaneously, rather than the average value, or in addition to the same. Or, provisions could be made to set by means of a manually actuated switch whether to have the display member show the value of oxygen saturation averaged over the two light receivers and their associated measurement channels, or to show the oxygen saturation value calculated on the basis of the signals emitted by the one or the other light receiver. The time dependent selection of the signals used for calculating the oxygen saturation will be explained later in more detail.

Let mention be made here of the possibility to equip the apparatus 61 with one additional switch to select the operational mode. Thus two additional keying switches could be provided for predetermining whether the system should compute the oxygen saturation as described, on the basis of reflection light and transmission light received simultaneously by the light receivers, or else on the basis of reflection light only, or on the basis of transmission light only. If one of the two modes of operation has been preselected, in which mode the oxygen content is to be calculated, i.e. either on the basis of reflection light only or on the basis of transmission light only, then the controlling device may be arranged to exert control over the light sources supply devices 85—at least in the case of these two modes of operation—to have the light signals generated by the light sources of one measuring head 23 fall into the time spaces between the light signals generated by the light sources of the other measuring head. The controlling device 83 will then also be capable—by means of the previously mentioned and/or additionally provided electronic pathways—to differentiate between the light signals generated by reflection light and the light signals generated by transmission light, and to sort them out on the basis of their time sequenced arrival.

Figure 5:
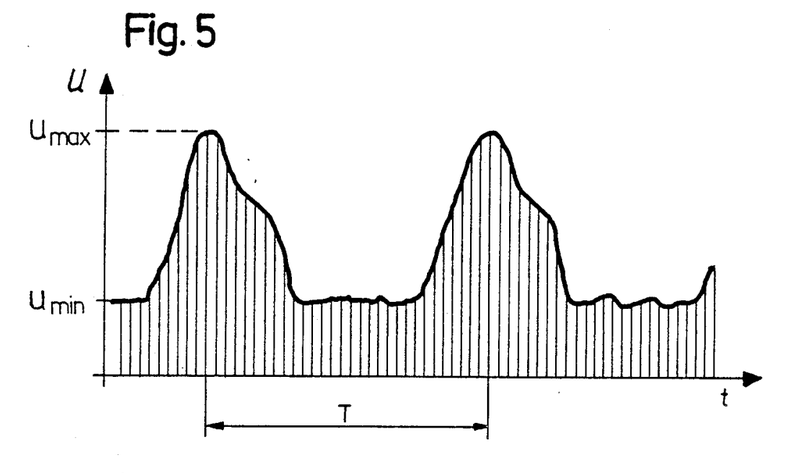
FIG. 5 shows a graph illustrating the time dependent variation of the signals generated by a light receiver of the system adapted to receive light of a predetermined wave length.

The blood oxygen saturation as existing during the optical measurement in the examined region of the bodily part 1 changes with the beat of the heart pulse and reaches a maximum each time a surge of fresh blood is pumped. The absorption of light having at least approximately the isobestic wave length is at least approximately independent of the variation of oxygen saturation that takes place at the rhythm of the heart pulse. On the other hand, for light having a wave length deviating considerably from the isobestic wave length and which correspondingly is absorbed at different rates by hemoglobin containing or lacking oxygen, the absorption varies with the rhythm of the heart pulse, so that the light intensity becomes modulated by the heart pulse waves. At each surge of freshly arriving blood the absorption will thus have either a maximum or a minimum, and so will the permeated light or the light dispersed back. In the following it will be assumed, that the light sources 35—as mentioned before—generate light having a wave length near the isobestic wave length, for example 830 nm, and the light sources 37 generate light at a wave length lying clearly below the isobestic wave length, for example at 670 nm. This light generated by the light sources 37 will then be absorbed with less strength than the light generated by the light sources 35. The diagram shown in FIG. 5, in which the time is plotted on the abscissa, schematically shows the time dependent variation of the voltage U of the pulse-shaped electrical signals generated by one of the two light receivers 33 in response to the light generated by the light sources 37 which permeates it. The envelope of the signals or pulses possesses for each wave of the human pulse, i.e. for every heartbeat, a maximum voltage value $U_{max}$, and displays a drop to a more or less plateau-shaped minimum of a voltage value $U_{min}$ between successive maxima. The duration of a pulse period between two heartbeats is indicated by T in FIG. 5. The oxygen saturation which—as already mentioned—changes congruent with the heartbeat, has a variation similar to that shown in FIG. 5 and possesses a maximum each at the values $U_{max}$. According to the usual practice this maximum value of oxygen saturation shall be displayed by the display member 63 as being the result of the measurement. The controlling device 83 therefore comprises—in its part that works in analog and/or digital manner—means for sorting out the signals having voltage values $U_{max}$, and to utilize them for the calculation of the oxygen saturation. The controlling device 83 may comprise circuit means adapted to work for example as a PLL-control circuit, i.e. as a phase-locked control circuit, adapted to temporarily open a gate each time the voltage U attains the maximum value $U_{max}$. The controlling device 83 is furthermore adapted to determine the duration of the period T, to compute therefrom the heart pulse frequency and to feed the corresponding signals to the display member 63, to make it display the heart pulse frequency. Evidently, the controlling device 83 also performs some averaging operations to balance out fluctuations in the measured values.

The ultrasonic generators 87 are adapted to supply energy to the piezoelectric ultrasonic radiators 39, to make the latter carry out mechanical vibrations at frequencies lying for example within the range of 0.5 to 5 MHz and to emit ultrasonic waves. Together with the associated radiator 39 the generators 87 are capable of forming an electrical oscillator vibrating with the resonant frequency of the radiator 39. If it is desired to have the ultrasonic waves generated by the ultrasonic radiators pertaining to the same measuring head possess the same frequencies and phase angles to avoid interferences, then the associated generators 87 may be accordingly controlled by the controlling device 83 and/or directly coupled with each other, with the consequence that the radiators 39 will possibly vibrate at frequencies deviating somewhat from their resonant frequencies. Instead or in addition to this, it would be equally possible—for reducing interferences—to subdivide the hollow spaces of the measuring heads 23 that contain the gelatinous mass serving as the ultrasonic transmitter 45 into sectors by separating walls, such sectors to be associated with each ultrasonic radiator 39.

The ultrasonic waves generated by the ultrasonic waves 39 are transmitted by the ultrasonic wave transmitters 45 to the bodily part 1, said transmitters being adapted to also serve particularly for matching the wave resistance of the radiator to that of the bodily part 1. The ultrasonic waves will permeate the bodily part 1 and heat it. In this way it will be possible to heat the blood vessels containing regions of the skin sections which the measuring heads are in contact with, and maybe even the blood vessels containing tissue sections lying below said skin sections, to a certain temperature, without risking the outermost skin layers lacking blood vessels to be heated above said certain temperature, but instead having them remain, in general, below this temperature. The heating of the blood vessels containing bodily regions and tissues increases their blood supply, which in turn increases the influence of the light radiated into the bodily part 1, as caused by the hemoglobin of the blood.

The electronic controlling device 83 will now exert control over the generators 87 to have them switched on and off in pulses, and will control the time duration or the widths of these pulses. The radiators 39 will correspondingly radiate the ultrasonic wave in pulses or packs. The frequency of these ultrasonic wave pulses or packs is considerably larger than the heart pulse frequency and is held by the controlling device 83 at a constant value, for example lying between a minimum of 300 Hz and a maximum of 400 Hz. The controlling device 83 controls the pulse width of the ultrasonic wave pulses and at the same time the power output radiated by the radiators 39 in a way to have the difference between the voltage values $U_{max}$ and $U_{min}$, or the ratio between this difference and the value of $U_{min}$ or $U_{max}$ be equal to a predetermined desired value or at least will lie within a predetermined desired range. Since the light receivers 33 of both measuring heads deliver electrical signals which define values of $U_{max}$ and $U_{min}$, and since the values $U_{max}$, $U_{min}$ of the two measuring channels are, in general, different from each other, the controlling device 83 may be quipped for example to average out the differences $U_{max}-U_{min}$ calculated from the signals originating from the light receivers of the two measuring heads, or to average out the ratios between these and $U_{min}$ or $U_{max}$. Provision may also be made, however, to have the controlling device 83 utilize only the voltage value differences originating only from one of the two measuring heads for its controlling function. Furthermore, there exists the possibility to equip the apparatus 61 with at least one switch to serve for preselecting whether the signals originating from one or from both measuring heads shall be utilized for controlling the ultrasonic power output. Furthermore, this control could be exerted not on the basis of said voltage differences or said ratios but on the basis of other variables selected to represent a measure for the size or intensity of the change produced by the heart pulse in the reflection and/or transmission light radiated out from a region of the body. This control could be exerted for example on the basis of values of oxygen saturation to be calculated for the maximum values of the heart pulse wave and for intermediate locations. If light having a wave length lying above the isobestic wave length were used for controlling the radiation, then the curve corresponding to the envelope shown in FIG. 5 would have its peaks, caused by the heart pulse, not looking upward, but rather downward.

As will be explained in further detail, the system may be designed for measuring oxygen saturation at various parts of the body and for various modes of operation. Thus provision could be made, to equip the apparatus 61 with an adjusting member adapted to fit the desired value required for the control of the power output, to the various measurement locations and modes of operation.

The described control of the power output emitted by the ultrasonic radiators 39 enables the bodily regions examined with optical measurement techniques to be heated to a temperature guaranteeing acceptable accuracy of measurement, such temperature being allowed to amount to not more than or approximately 41° C., for example. In order to avoid cell damages should a disturbance in the controlling process arise, the apparatus 61 may be equipped with means to keep the ultrasonic power output below a limit value.

Figure 6:
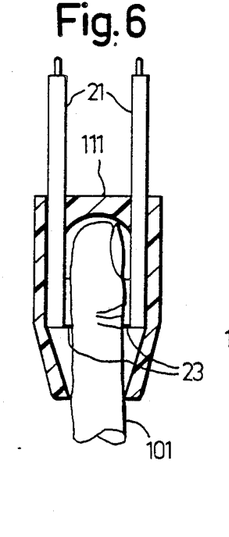
FIG. 6 shows a section through a variant of the mounting device.
Figure 7:
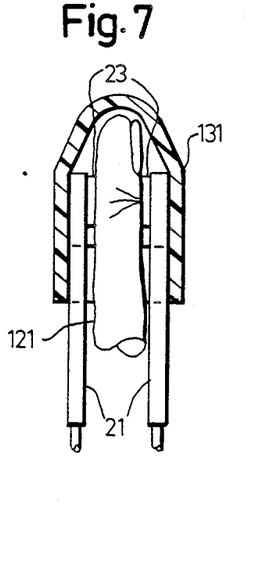
FIG. 7 shows a section through another variant of the mounting device.

As mentioned before, the bodily part 1 to be examined may be an ear lobe. The system may also be used to measure—in analogous fashion—the oxygen saturation of blood of other bodily parts, such as the tongue, the nose, a cheek, a finger or a toe. Since the thickness of these bodily parts may lie outside the range within which the distance of the contact surfaces—facing each other—of the two measuring heads 23 may varied, or because it may be otherwise of advantage to provide different mounting devices to be used for other bodily parts, the system may be equipped with mounting devices of various dimensions and/or shapes, onto which the holding members 21 may be detachably mounted, as required. FIGS. 6 and 7 show for example the fingers 101 and 121 having the mounting devices 111 and 131, respectively, placed thereonto. A mounting device of this kind consists essentially of a thimble-like cap provided for example with longitudinal slots and having slightly spring-like elastic qualities, and consisting for example of a plastic material. The holding members 21 may be detachably fastened onto the mounting devices 111, 131 in a way to have the front faces of the measuring heads 23 adapted for light emission and reception arranged to face toward each other, as shown in the arrangement of FIG. 1. Correspondingly, the measuring process may be performed with the arrangements of FIGS. 6 and 7 in a manner similar to that explained in conjunction with the arrangement shown in FIG. 1.

Figure 8:
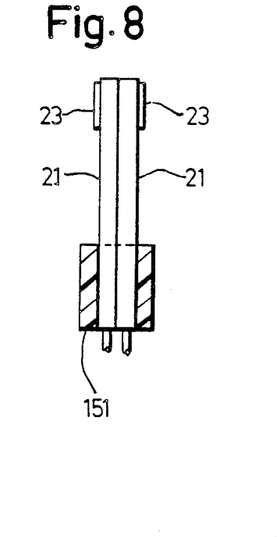
FIG. 8 shows a section through a further variant of the mounting device.

The mounting device 151 according to FIG. 8 essentially consists of a block provided with a through hole, the block consisting for example of a plastic material. The holding members 21, rectangular in cross-section, may be inserted snugly into said through hole in a way to have their rear surfaces facing away from the measuring heads which protrude from said holding members 21 abut against each other. Correspondingly, the front faces of the measuring heads 23 adapted for emitting and receiving light will face away from each other too. The holding members 21 and the measuring heads arranged in this way may be used for example to perform a measurement in the inside of a bodily opening. The measurement heads may be introduced for example into the mouth, into the area between the underside of the tongue and the bottom of the mouth located below, or into the anal region. In such an arrangement of the measuring heads the light receivers can evidently receive from the bodily region examined no transmission light, but only reflection light. However, in this case too, the two measuring heads working parallel to each other yield better and more accurate measurement results, than would be the case with a single measuring head.

It is furthermore possible to perform measurements with both measuring heads at the same time at different parts of the body located relatively far from each other, for example on the upper and the lower arm. Such measurements supply information as to the spread of the heart pulse waves and the oxygen transport tied in therewith. Furthermore it is also possible to apply only one of the two measuring heads to a particular bodily part, to measure there the oxygen saturation. For applications of this kind the display member would show—as has been mentioned before as a possibility—the oxygen saturation computed individually for one or for each light receiver, rather than the oxygen saturation value averaged over the two light receivers.

Figure 9:
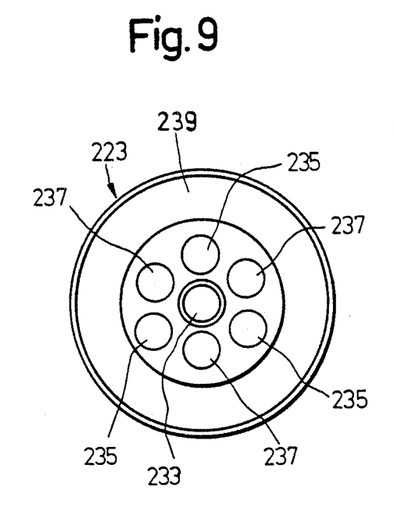
FIG. 9 shows a top view corresponding to FIG. 3 of a variant of the measuring head.

Also the two measuring heads 23 may be replaced by modified measuring heads. For example, in conjunction with the measuring head 223 shown in FIG. 9 there could be provided six light sources uniformly distributed on a circle around a light receiver 233, the three light sources 235 being arranged to generate light of a predetermined wave length, and the three light sources 237 to generate light of a different wave length. As another possibility the six light sources could be subdivided into three pairs, each of which would generate light of a different wave length, so that light would be generated at three different wave lengths. The electronic controlling device could be modified in this case to make it compute the oxygen saturation from light intensities of light signals having three different wave lengths. The measuring head 223 comprises only one single ultrasonic radiator 239 implemented as a circular piezoelectric plate arranged to enclose the light receiver 233 and the six light sources 235, 237. The ultrasonic radiator 239 may be controlled in a manner similar to that explained in conjunction with the ultrasonic radiator 39.

The measuring heads may have an elongated shape rather than a circular perimeter. In this case, the light receiver and two or three pairs of light sources and one pair of ultrasonic radiators may be arranged in a straight row, the light receiver being located in the center of this row.

Figure 10:
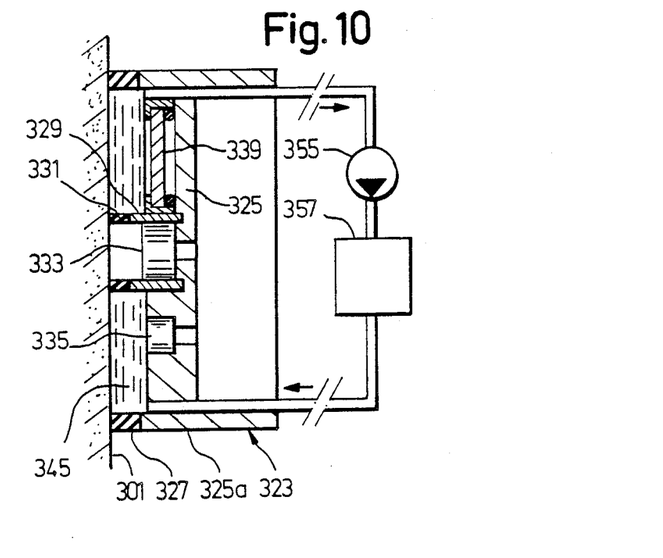
FIG. 10 shows a schematic section of a further variant of the measuring head.

FIG. 10 shows a piece of skin 301 and a measuring head 323 making contact therewith and possessing for example a circular perimeter. The measuring head 323 comprises a support 325 with a cylindrical shell 325a provided at its end adjacent to the skin with a gasket 327 consisting for example of liquid tight foam rubber. A sleeve 329 is fixedly mounted in the central region of the support 325 and provided at its end adjacent to the skin with a gasket 331 also preferably liquid tight, the sleeve 329 being arranged to accommodate a light receiver 333. The measuring head 323 further comprises light sources 335 and ultrasonic radiators 339, in an arrangement similar to that of the measuring head 23, for example. The measuring head 323 differs, however, from the measuring head 23 in that instead of a gelatinous ultrasonic wave transmitter it comprises an ultrasonic wave transmitter 345 consisting of a transparent liquid, such as water. After arranging the measuring head 323 liquid tight on the skin 301, the liquid may be pumped into the hollow space—adjacent to the skin—of the measuring head, by means of a pump 355 and continuously circulated through a temperature control device 357 adapted to hold the liquid temperature constant. When the inner region of the skin comprising blood vessels and perhaps the tissue located underneath become heated in the course of a measurement by the emission of ultrasonic waves, the skin surface may get cooled and held at a temperature lying below the temperature of the inner body regions containing the blood vessels and heated by the ultrasonic waves, said temperature being arranged to correspond to the normal body temperature.

Figure 11:
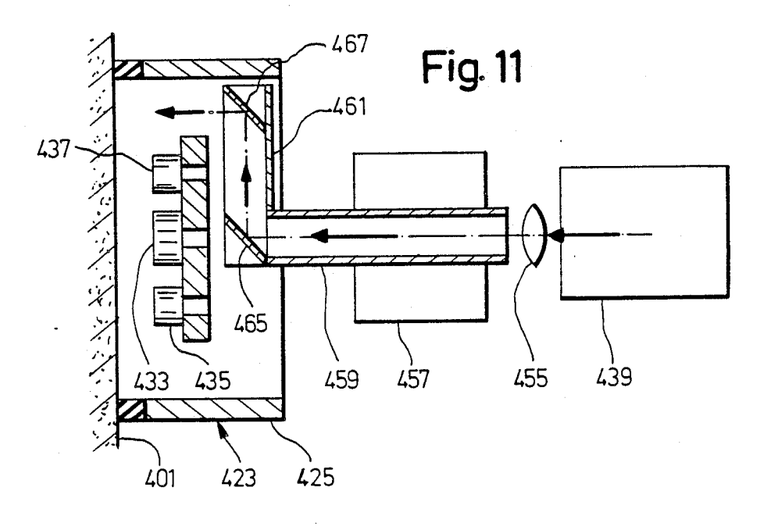
FIG. 11 shows a schematic section through still another variant of the measuring head.

FIG. 11 shows a measuring head 423 of circular perimeter in contact for measurement with the skin 401 and comprising a support 425. The support 425 in turn comprises a light receiver 433 and the light sources 435, 437 implemented as photodiodes and distributed around the light receiver. Thus for example, three light sources 435 could be arranged to generate light of one predetermined wave length, and three light sources 437 for generating light of a different wave length.

A gallium-aluminum-arsenic laser diode adapted to generate light of a wave length of at least 600 nm, by preference at least 800 nm, not more 1600 nm and preferably not more than 1200 nm, is provided as a light radiator 439, specifically as an infrared light radiator, this light radiator being either fastened directly to the measuring head 423 or inside the same, or optically connected therewith by way of a light conductor. The measuring head is furthermore equipped with an electric motor 457, specifically a micromotor, comprising a hollow shaft 459 coaxial with the central axis of the measuring head, the radiator 439 being adapted to send light into said hollow shaft 459 from the side facing away from the skin 401, by way of a light beam spreader 455. At the hollow shaft end located nearer to the skin 401 is fixedly mounted an arm-shaped light diverter 461, which protrudes radially outwardly and away from the hollow shaft. This light diverter 461 which, together with the radiator 439 constitutes the radiating and heating means, is provided at its end with one reflector each, 465 and 467, respectively. These reflectors 465, 467 enable the light radiated through the hollow shaft by the radiator 439 to be diverted first radially outwardly and away from the hollow shaft 459 and toward the surface of the skin 401. If during measurement the light diverter 461 is rotated by the motor 457 at a rotational speed having a value of preferably not less than 100 rpm, and for example not less than 300 rpm, then the light beam radiated by the radiator 439 and diverted by the reflectors 465, 467 strikes upon a circular area of the skin surface and penetrates through the latter into the inner skin layer comprising blood vessels, and into the tissue lying below. The epidermis is of comparatively good permeability for infrared light having wave lengths between 800 nm and 1600 nm. In contrast thereto, blood absorbs that kind of light with relative strength, with the result that the blood flowing through the capillaries and through the other blood vessels in the irradiated region of the body, as well as the close environment thereof, will become heated. The second measuring head of the system may evidently be built identical.

The light generated by the light radiators 439 of each of the two measuring heads advantageously possess a wave length different from the wave length of the light produced by the light sources 435 and 437. The electronic controlling device of the apparatus that corresponds to the apparatus 61 is adapted to turn on the light sources 435, the light sources 437 and the light radiators 439 of the two measuring heads pulsatingly and in alternating cycles. The frequency of these pulse sequences may lie in the same range as has been specified for the light sources 35, 37, or it may be higher and lie for example in the same frequency range as has been specified for the ultrasonic pulses. In addition to the light signals emitted by the light sources 435, 437 the light receiver of each measuring head also receives reflection light signals and—in case of proper arrangement of the two measuring heads—transmission light signals generated by the light radiator 439 of the measuring head or heads. The controlling device may now calculate the oxygen saturation either on the basis of lights signals emitted by the light sources 435 and 437 alone, or it may utilize therefor those light signals too, that originate from the light radiator 439, or from the light radiators of both measuring heads.

As an alternative, provision could be made to distribute around the light receiver 433 one single type of photodiode to serve as light sources, all of which would produce light of the same wave length. In this case, the oxygen saturation could be calculated on the basis of light signals having two different wave length, as originating from the light sources and from the light radiator 439.

The controlling device controls the power output irradiated by the light radiator 439 of each measuring head in the form of infrared waves, by pulse width control, in a manner analogous to that described in conjunction with the control of the radiation output of the ultrasonic waves.

In order to be able to adequately heat a bodily region for measurement purposes, it is necessary to supply the laser diode with an electrical power output for example of a magnitude of $0.5 \pm 0.2 W/cm^2$ averaged over the pulse sequence. If the measuring head has a diameter of approximately 2 cm and correspondingly covers a skin surface of the order of magnitude of 3 $cm^2$, then the power output required lies in the order of magnitude of 1 to 2 mW. It is possible to use as infrared light radiator 439 a laser diode have a nominal power output of 5 mW under conditions of continuous operation, or for example of not more or approximately 10 mW, and then to control the width of the generated infrared pulses in such a way, that the power output averaged over the pulse sequence will have the required value to guarantee an adequate heating of the tissue.

It is worth mentioning in this connection, that the light sources 435, 437 implemented as photodiodes that generate conventional—i.e. incoherent—light, evidently also irradiate the skin with energy in the form of electromagnetic waves. However, the photodiodes commonly serving for the optical measurement of oxygen saturation typically have nominal power outputs of less than 0.1 mW, while the actual average electrical power consumption is even smaller because of the pulse-wise operation, so that this sort of light radiation results in practically no noticeable heating of the tissue. However, it is possible to provide—instead of the light radiators 439 consisting of laser diodes and the means for diverting the light beam originating therefrom—several laser diodes of sufficient power output, or else to provide conventional photodiodes producing incoherent light and arranged around the light receiver, and to control their power output by pulse width control. Depending on the number of available laser diodes or photodiodes, each of these could have for example a nominal power rating of at least 1 mW at continuous operation, so that the power consumption of the totality of diodes averaged over the pulse sequences and referred to the bodily surface covered by the measuring head will amount to not less than about 0.5 $mW/cm^2$. The light pulses generated by the laser diodes or by the common diodes could then serve at the same time for the measurement of oxygen saturation.

It would be possible, furthermore, to equip each measuring head with more than one light receiver. Each measuring head could be provided for example with two photodiodes, each of which to be photosensitive only within a narrow rage of wave lengths. One of these photodiodes would then respond to light of a wave length generated by one of the groups of light sources, the other photodiode would respond to light of a wave length generated by the other group of light sources.

Furthermore it would be possible to equip each measuring head with a single light source for each light wave length to be generated for amusement purposes.

Also, the described systems could be used for measuring the oxygen saturation not only in human blood, but also in the blood of animals.

If a system is provided for making measurements with reflection light only, then it could be equipped with a single measuring head.

Obviously, numerous modifications and variations of the present invention are possible in the light of the above teachings. It is therefore to be understood that within the scope of the appended claims the invention may be practiced otherwise than is specifically described herein.

Accordingly, what is claimed is:

1. System for the measurement of the content of a gas in the blood of a living being in a region of the body thereof, the system comprising:
   radiation means adapted to radiate waves into the region of the body for heating the region;
   controlling means provided for controlling the power output of the waves radiated by said radiating means;
   at least one light receiver for optically measuring the gas, and wherein said controlling means are adapted to control said radiating means in a way to have a value representing a measure for the changes in the intensity of light emitted from the bodily region and received by said light receiver which, at least one of, lie within a predetermined desired value range and equal a desired value.

2. System as claimed in claim 1, where said controlling means are further adapted such that said value represents a measure for light intensity changes caused by the pulse of the living being subjected to the measurement process.

3. System as claimed in claim 1, wherein said radiating means comprises at least one ultrasonic radiator.

4. System as claimed in claim 1, further comprising at least one measuring head provided with light emitting means for emitting light of various wave lengths directed toward said region of the body and serving for the optical measurement of the blood gas with at least one light receiver, the measuring head further comprising wall means bounding a hollow space provided on the side of the measuring head and destined to make contact with a bodily part during measurement, and a pump being provided for pumping liquid through said hollow space.

5. System as claimed in claim 4, wherein said pump and said hollow space are arranged to form a circuit.

6. System as claimed in claim 4, comprising a temperature control device adapted to control the temperature of said liquid.

7. System as claimed in claim 4, wherein said radiating means comprise at least one ultrasonic radiator and wherein the latter and said hollow space are so arranged, that during the measuring process at least some part of the hollow space is located between the ultrasonic radiator and the bodily part, and wherein liquid provided in said hollow space is adapted to transmit onto the bodily part ultrasonic waves generated by said ultrasonic radiator and is adapted to match the wave resistance of the ultrasonic radiator to the wave resistance of the bodily part.

8. System as claimed in claim 1, wherein said radiating means are adapted for radiating pulsed waves.

9. System claimed in claim 1, wherein said controlling means are adapted for pulse width control of the radiated waves.

10. System for the optical measurement of oxygen saturation of blood in a region of the body of a living being, the system comprising:
    two measuring heads, each of which being provided with light emitting means adapted to emit light of various wave lengths;
    at least one light receiver;
    a mounting device adapted to detachably support the two measuring heads; and
    at least one additional mounting device equally adapted to datachably support the two measuring heads, said mounting device and said at least one additional mounting device being of dissimilar construction, thereby enabling the two measuring heads to be mounted as required onto the various mounting devices in different positions in relation to each other whereby the different positions depend on the specific mounting device selected.

11. System as claimed in claim 10, wherein at least two dissimilar mounting devices are adapted to support the measuring heads in a way to have their sides serving for emitting and receiving light to be disposed on opposing sides of a bodily part and arranged to face each other.

12. System as claimed in claim 10, wherein at least one mounting device is adapted to support the two measuring heads in a way to have their sides serving for emitting and receiving light disposed on opposing sides of a bodily part and arranged to face each other, another mounting device being adapted to support the measuring heads to have their sides serving for emitting and receiving light face away from each other.

13. System as claimed in claim 10, wherein each measuring head is fastened onto one end of an elongated holding member detachable connectable with at least some of the mounting devices in a way to have its side serving for emitting and receiving light define a plane parallel to the longitudinal direction of the holding member.

14. System for the optical measurement of oxygen saturation of blood in a region of the body of a living being, the system comprising:
    two measuring heads, each of which being provided with light emitting means adapted to emit light of various wave lengths;
    at least one light receiver; and
    electronic circuit means connected to said measuring heads to process electrical signals supplied by said at least one light receiver to determine therefrom the oxygen saturation, wherein said circuit means are adapted to utilize light which originates from the light emitting means pertaining to the same measuring head as the light receiver which receives said light does, as well as light received by the light receiver in question and originating from the light emitting means of the other measuring head.

15. System for the optical measurement of oxygen saturation of blood in a region of the body of a living being, the system comprising:
   two measuring heads, each of which being provided with light emitting means adapted to emit light of various wave lengths;
   at least one light receiver; and
   electronic circuit means electrically connected with said measuring heads to process electrical signals supplied by the light receiver to said measuring heads and to determine therefrom the oxygen saturation, wherein at least when the two measuring heads are positioned on opposing sides of a bodily part, said circuit means is adapted to determine the oxygen saturation on the basis of the electrical signals supplied to said circuit means by said light receivers of both said measuring heads.

16. System for the measurement of the content of a blood gas, the system comprising:
   at least one measuring head, for measuring said gas content optically, comprising a support, a shell disposed on the support, at least one light receiver, and at least one light source, the shell surrounding said at least one light receiver and said at least one light source, said measuring head being adapted to contact a bodily part and being open on the side designated to contact said bodily part wherein an edge of the shell designated to contact said bodily part is provided with a gasket of rubber-like elastic material; and
   at least one ultrasonic radiator, also disposed within the shell and adapted to radiate ultrasonic waves into a region of the bodily part.

17. System for the measurement of the content of a blood gas, the system comprising:
   at least one measuring head for measuring said gas content optically comprising a support, a shell, disposed on said support, at least one light receiver, and at least one light source, the shell surrounding said at least one light receiver and said at least one light source, said measuring head being adapted to contact a bodily part and being open on the side designated to contact said bodily part; and
   at least one ultrasonic radiator comprising a plate-shaped, piezoelectric element, also disposed within the shell and adapted to radiate ultrasonic waves into a region of the bodily part, and
   an ultrasonic wave transmitter consisting of a gelatinous mass disposed in a space enclosed by the shell on that side of the piezoelectric element that is designated to face the bodily part.

18. System as claimed in claim 17, wherein said gelatinous mass is pervious to visible and infrared light.

19. System for the measurement of the content of a blood gas, the system comprising:
   at least one measuring head, for measuring said gas content optically, adapted to contact a bodily part, said at least one measuring head including a support, at least one light receiver, at least one light source and ultrasonic radiators, adapted to radiate ultrasonic waves into a region of the bodily part arranged on opposite sides of the at least one light receiver;
   said at least one light receiver, said light source, and said ultrasonic radiators being supported by said support.

* * * * *